(12) United States Patent
Shigaraki

(10) Patent No.: US 8,225,540 B2
(45) Date of Patent: Jul. 24, 2012

(54) WRISTBAND AND USE METHOD THEREOF

(75) Inventor: Yoshio Shigaraki, Tokyo (JP)

(73) Assignee: Sato Holdings Kabushiki Kaisha (JP)

( * ) Notice: Subject to any disclaimer, the term of this patent is extended or adjusted under 35 U.S.C. 154(b) by 511 days.

(21) Appl. No.: 12/521,175

(22) PCT Filed: Dec. 20, 2007

(86) PCT No.: PCT/JP2007/074578
§ 371 (c)(1),
(2), (4) Date: Jun. 25, 2009

(87) PCT Pub. No.: WO2008/078659
PCT Pub. Date: Jul. 3, 2008

(65) Prior Publication Data
US 2010/0045022 A1 Feb. 25, 2010

(30) Foreign Application Priority Data

Dec. 25, 2006 (JP) .................................. 2006-347884
Dec. 25, 2006 (JP) .................................. 2006-347885

(51) Int. Cl.
*A44C 5/00* (2006.01)
(52) U.S. Cl. .......................................... 40/633; 40/665
(58) Field of Classification Search .................. 40/633, 40/665; 600/587; 63/3–3.1
See application file for complete search history.

(56) References Cited

U.S. PATENT DOCUMENTS

| | | | | |
|---|---|---|---|---|
| 1,857,523 A | * | 5/1932 | Wittel | 33/561.2 |
| 3,292,261 A | * | 12/1966 | Hayes | 33/2 R |
| 4,428,385 A | * | 1/1984 | Morales | 600/587 |
| 4,875,296 A | * | 10/1989 | Holzmeister et al. | 33/770 |
| 5,377,691 A | * | 1/1995 | Boileau et al. | 600/587 |
| 5,448,846 A | * | 9/1995 | Peterson et al. | 40/633 |
| 5,452,523 A | * | 9/1995 | Jansen | 33/555.4 |
| 5,774,999 A | * | 7/1998 | Smith | 33/555.4 |
| 2006/0179542 A1 | | 8/2006 | Pierce | |

FOREIGN PATENT DOCUMENTS

| | | |
|---|---|---|
| JP | 2003-164307 A | 6/2003 |
| JP | 2004-242904 | 9/2004 |
| JP | 2006-58805 A | 3/2006 |

OTHER PUBLICATIONS

International Search Report dated Feb. 5, 2008, issued in corresponding international application No. PCT/JP2007/074578.

* cited by examiner

*Primary Examiner* — Casandra Davis
(74) *Attorney, Agent, or Firm* — Ostrolenk Faber LLP

(57) ABSTRACT

A wristband that can be attached comfortably to wrists or ankles of various sizes by adjusting a band length. The wristband includes: a display portion, a band portion in a first end portion of the wristband as an extension from one side of the display portion; the first end portion includes band holes, and is wrapped around a wrist or the like; a setting portion formed in the other end portion as an extension from the other side of the display portion, includes a setting hole, and is overlapped with the band portion to attach the wristband in loop form. Band hole displays are printed beside the band holes in positions corresponding to the respective band holes. Band hole displays constituted by the same sequence of numbers as the band hole displays are provided beside the band holes, and boundary marks indicating the application range of the corresponding band hole display are provided in a length measurement portion at identical intervals to the band holes.

16 Claims, 11 Drawing Sheets

WRISTBAND AND USE METHOD THEREOF

CROSS REFERENCE TO RELATED APPLICATION

The present application is a 35 U.S.C. §§371 national phase conversion of PCT/JP2007/074578, filed Dec. 20, 2007, which claims priority of Japanese Application No. 2006-347884, filed Dec. 25, 2006, and Japanese Application No. 2006-347885, filed Dec. 25, 2006, the disclosures of which are incorporated by reference herein. The PCT International Application was published in the Japanese language.

BACKGROUND OF THE INVENTION

1. Field of the Invention

The present invention relates to a wristband that is used to display information when wrapped in loop form around and latched to a wrist, an ankle, or the like in a hospital, an amusement park, and so on, and a use method thereof.

2. Description of the Related Art

In recent years, wristbands have come to be used in hospitals, amusement parks, and so on to display patient information, facility use information, and so on. To describe a conventional wristband 51 with reference to FIG. 11, the wristband 51 has a display portion 52 formed in a lengthwise direction center of a strip-form base material, a band hole 53 formed in one end portion of the wristband 51 on one side of the display portion 52, and a setting hole 54 formed in the other end portion of the wristband 51 on the other side of the display portion 52. In a hospital, for example, required information relating to a patient or the like, such as a name and an ID number, is printed on the display portion 52 by a printer, whereupon the wristband 51 is attached to the wrist of the patient or the ankle of a newborn baby. During drug administration, treatment, and so on, the display content on the display portion 52 is compared with the written content of a medical chart to make sure that there are no errors in the content of the drug administration and treatment applied to the patient or the like. The wristband 51 is attached to the wrist or the like in loop form by inserting a specialized clip into the band hole 53 and the setting hole 54 and latching the band hole 53 and setting hole 54 with the clip. To ensure flexibility in relation to various sizes of wrist, a plurality of band holes 53 are typically provided in the lengthwise direction, and the band hole 53 in an appropriate position is selected in accordance with the size of the wrist or the like. Thus, the diameter of the wristband 51 can be adjusted. In other words, by varying the band hole 53 appropriately, the wristband 51 can be attached at an appropriate circumference within a range that is larger than the circumference of the wrist (a short circumference part) and smaller than the circumference of the palm of the hand (long circumference part) to ensure that the wristband 51 does not fall off the wrist, and thus the wristband 51 is neither too loose nor too tight.

Conventionally, however, the length of the wristband is adjusted during attachment in accordance with the experience of the operator or through visual measurement, and therefore, when attachment is performed in a situation where children and adults having different wrist sizes are present or the like, irregularities may occur depending on the experience of the operator, leading to variations in comfort of use such as excessive tightness and excessive looseness.

Patent Document 1: Japanese Unexamined Patent Application Publication 2004-242904[i].

[i] It appears that this reference document is not mentioned in specification.

SUMMARY OF THE INVENTION

The present invention has been designed in consideration of this problem, and an object thereof is to provide a wristband that can be attached comfortably to wrists or ankles of various sizes, such as the wrists and ankles of children and adults, by adjusting a band length easily and quickly, and a use method thereof.

To solve the problem described above, in a wristband according to a first invention, a plurality of band holes are formed at predetermined intervals in one lengthwise direction end portion of a strip-form base material, a center of which serves as a display portion, and a setting hole is formed in another end portion. The wristband is attached in loop form to a wrist or an ankle by inserting a wristband clip into the band hole and the setting hole. The wristband includes aligning means for matching a length between the setting hole and a band hole to be used to a circumference of an attachment subject wrist or ankle.

In a second invention, a length measurement portion is provided in the aligning means on a parallel line to the band holes in the one end portion, the band holes being respectively associated with the length measurement portion such that the band holes can be referenced individually, and an interval from each of the band holes to the setting hole is set to be longer, by a predetermined length, than an interval from the length measurement portion corresponding to the respective band holes to a starting point portion set in the other end portion on a line of extension from the length measurement portion.

Further, a band hole display constituted by a number, a symbol, or the like may be provided in the vicinity of each of the band holes to identify the respective band holes, the band hole display may be provided in the length measurement portion, and the band holes and the length measurement portion may be associated referably via the band hole display.

Further, the band hole display provided in the length measurement portion may be defined by a boundary mark indicating a boundary thereof or by color coding.

Further, an interval from the starting point portion to a closest portion thereto of the length measurement portion may be set to be shorter than a minimum value of the circumference of the subject wrist or ankle, and an interval from the starting point portion to a farthest portion therefrom of the length measurement portion may be set to be longer than a maximum value of the circumference of the subject wrist or ankle.

Further, a difference between an interval from the band hole to the setting hole and an interval from the length measurement portion associated therewith to the starting point portion may be set to be smaller than a difference between a circumference of an individual subject wrist or ankle and a circumference of a hand or foot.

Further, the starting point portion may be a mark indicating a central position of the setting hole.

A method of using the wristband according to the second invention includes the steps of: overlapping the one end portion and the other end portion by wrapping the wristband around a wrist or an ankle; selecting the band hole display corresponding to the length measurement portion that overlaps the starting point portion at a minimum circumference; and latching the wristband to the wrist or ankle by inserting a wristband clip into the band hole corresponding to the selected band hole display and the setting hole.

In a wristband according to a third invention, the aligning means is constituted by a reference line provided in the other end portion at a predetermined distance from the band holes for comparing and verifying the circumference of the ankle or wrist between the band holes[ii], and an identification display portion provided in the direction of the setting portion from the reference line at a length that is equal to or greater than an interval between adjacent band holes so as to be identifiable through the band holes.

[ii] The precise meaning is not so unclear. See also Claim 9 and corresponding sections of specification.

Here, an interval between the band hole farthest from the setting hole and the reference line may be set to be larger than a maximum circumference of the attachment subject wrist or ankle.

Further, an interval between the band hole closest to the setting hole and the reference line may be set to be smaller than a minimum circumference of the attachment subject wrist or ankle.

Further, an interval between the setting hole and the reference line may be set to be smaller than a maximum-minimum circumference difference of a hand or a foot at which the wristband can be attached to a wrist or an ankle without falling off the hand or the foot.

Further, the interval between adjacent band holes may be set to be smaller than the interval between the setting hole and the reference line.

A method of using the wristband according to the third invention includes the steps of: overlapping the one end portion and the other end portion at a minimum circumference by wrapping the wristband around a wrist or an ankle; confirming the farthest band hole from the setting hole through which the identification display portion is displayed for identification; and latching the wristband to the wrist or ankle by inserting a wristband clip into the confirmed band hole and the setting hole.

The wristband according to the first invention is provided with the aligning means for matching the length between the setting hole and the used band hole to the circumference of the attachment subject wrist or ankle, and therefore, when the wristband is wrapped around the wrist or ankle, the position of the used band hole can be determined using the aligning means.

In the wristband according to the second invention, the length measurement portion is provided on a parallel line to the band holes in the one end portion, the band holes being respectively associated with the length measurement portion such that the band holes can be referenced individually, and the interval from each of the band holes to the setting hole is set to be longer, by a predetermined length, than the interval from the length measurement portion corresponding to the respective band holes to the starting point portion set in the other end portion on a line of extension from the length measurement portion. Therefore, by wrapping the wristband around the wrist or ankle such that the one end portion and the other end portion overlap, an appropriate band hole can be selected in combination with the setting hole from the length measurement portion that overlaps the starting point portion at the minimum circumference. As a result, adjustments can be made easily even by an operator having little attachment experience, and the wristband can be attached to the human body comfortably and quickly.

Further, by providing the band hole display constituted by a number, a symbol, or the like in the vicinity of each of the band holes to identify the respective band holes, providing the band hole display in the length measurement portion, and associating the band holes and the length measurement portion referably via the band hole display, the correct band hole can be referenced easily.

Further, when the band hole display provided in the length measurement portion is defined by the boundary mark indicating the boundary thereof or by color coding, an application range of the band hole display can be read easily.

Further, when the interval from the starting point portion to the closest portion thereto of the length measurement portion is set to be shorter than the minimum value of the circumference of the subject wrist or ankle and the interval from the starting point portion to the farthest portion therefrom of the length measurement portion is set to be longer than the maximum value of the circumference of the subject wrist or ankle, the wristband can be applied to all attachment subjects.

Further, when the difference between the interval from the band hole to the setting hole and the interval from the length measurement portion associated therewith to the starting point portion is set to be smaller than the difference between the circumference of an individual subject wrist or ankle and the circumference of a hand or foot, the wristband does not fall off the wrist or ankle.

Further, when the starting point portion is a mark indicating the central position of the setting hole, the starting point portion can be read easily.

The method of using the wristband according to the second invention includes the steps of: overlapping the one end portion and the other end portion by wrapping the wristband around a wrist or an ankle; selecting the band hole display corresponding to the length measurement portion that overlaps the starting point portion at a minimum circumference; and latching the wristband to the wrist or ankle by inserting a wristband clip into the band hole corresponding to the selected band hole display and the setting hole. Hence, an appropriate band hole interval can be selected in relation to wrists and ankles of various sizes, and therefore adjustments can be made easily even by an operator having little attachment experience, whereby the wristband can be attached to the human body comfortably and quickly.

In the wrist band according to the third invention, the reference line is set in the other end portion at a predetermined distance from the band holes for comparing and verifying the circumference of the ankle or wrist between the band holes, and the identification display portion is provided in the direction of the setting portion from the reference line at a length that is equal to or greater than an interval between adjacent band holes so as to be identifiable through the band holes. Therefore, by wrapping the wristband around the wrist or ankle such that the one end portion overlaps the other end portion, the identification display portion can always be identified through one of the band holes. Hence, by combining the band hole and the setting hole on the basis of a confirmation result of the identification display portion, the wristband can be attached to wrists and ankles of various sizes with a fixed, appropriate margin, and as a result, the wristband can be attached to the human body comfortably and quickly even by an operator having little attachment experience.

Further, when the interval between the band hole farthest from the setting hole and the reference line is set to be larger than the maximum circumference of the attachment subject wrist or ankle, the wristband can be attached to thick wrists and ankles.

Further, when the interval between the band hole closest to the setting hole and the reference line is set to be smaller than the minimum circumference of the attachment subject wrist or ankle, the wristband can be attached to thin wrists and ankles.

Further, when the interval between the setting hole and the reference line is set to be smaller than a maximum-minimum circumference difference of a hand or a foot at which the wristband can be attached to a wrist or an ankle without falling off the hand or the foot, the wristband does not fall off the wrist or ankle during use.

Further, when the interval between adjacent band holes is set to be smaller than the interval between the setting hole and the reference line, the wristband does not fall off the wrist or ankle during use.

The method of using the wristband according to the third invention includes the steps of: overlapping the one end portion and the other end portion at a minimum circumference by wrapping the wristband around a wrist or an ankle; confirming the farthest band hole from the setting hole through which the identification display portion is displayed; and latching the wristband to the wrist or ankle by inserting a wristband clip into the confirmed band hole and the setting hole. Hence, the wristband can be attached to wrists and ankles of various sizes with a fixed, appropriate margin, and as a result, the wristband can be attached to the human body comfortably and quickly even by an operator having little attachment experience.

DESCRIPTION OF THE PREFERRED EMBODIMENTS

Embodiments of the present invention will be described in detail below on the basis of the drawings.

Figure 1:
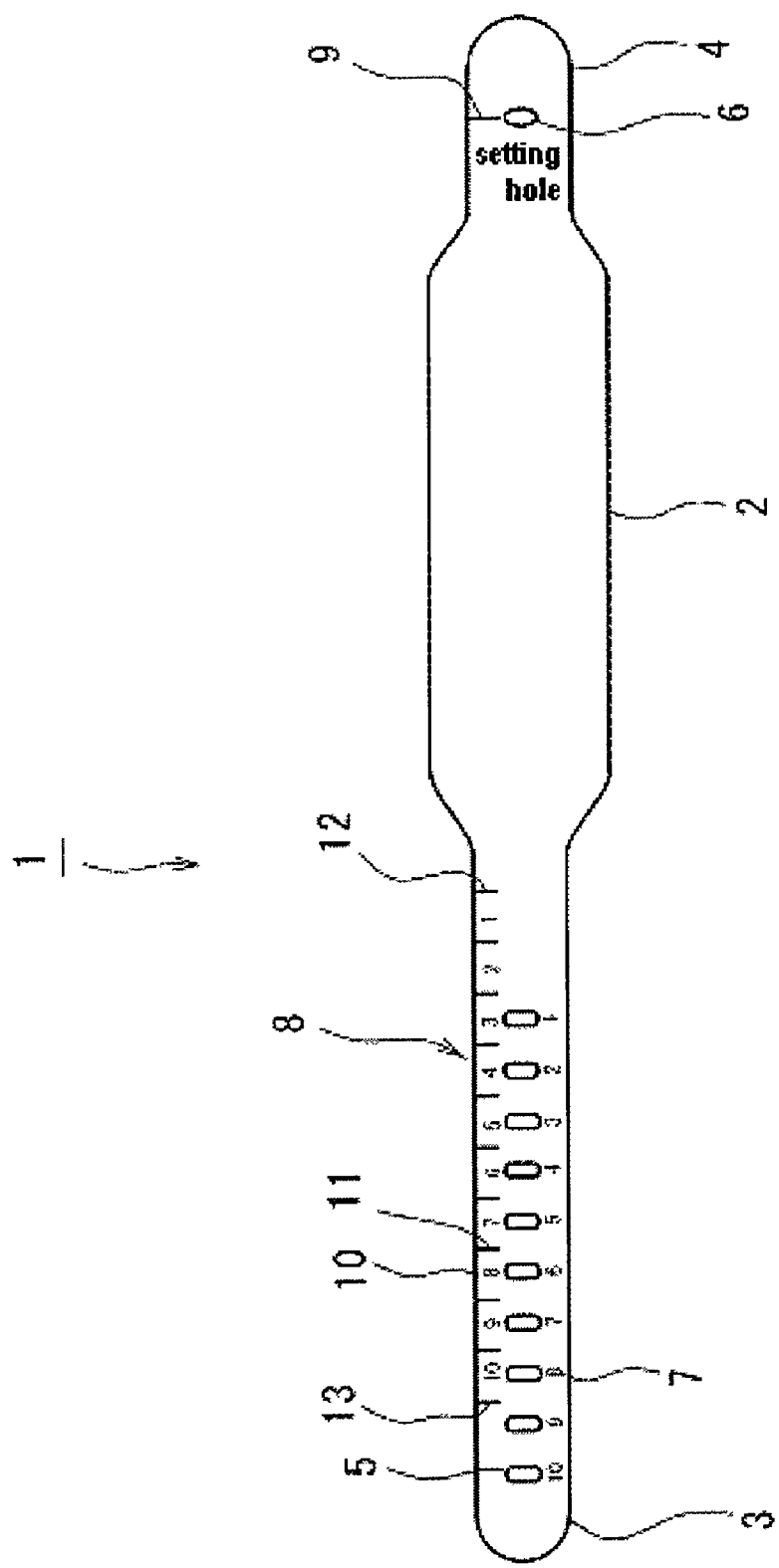
FIG. 1 is a plan view showing the constitution of a wristband according to a first embodiment of the present invention.
Figure 2:
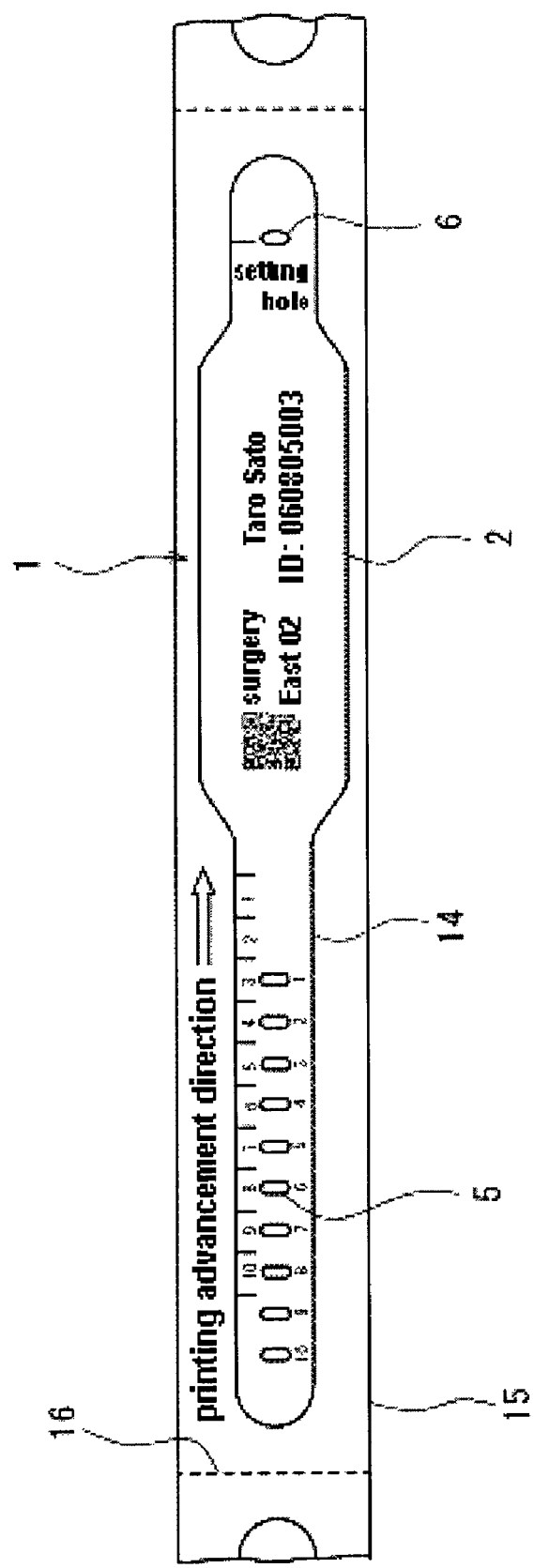
FIG. 2 is a plan view showing an example of use of the wristband shown in FIG. 1.

FIG. 1 is a plan view showing the constitution of a first embodiment of a wristband according to the present invention, and FIG. 2 is a plan view showing an example of use of the wristband shown in FIG. 1.

Referring to FIG. 1, a wristband 1 according to this embodiment is provided with a display portion 2, a band portion 3 that is formed on one end portion of the wristband 1 extending from one side of the display portion 2 and is wrapped around a wrist or the like, and a setting portion 4 that is formed on the other end portion of the wristband 1 extending from the other side of the display portion 2 and is overlapped with the band portion 3 to attach the wristband 1 in loop form. Ten band holes 5 are formed in the band portion 3 at equal lengthwise direction intervals, and a setting hole 6 is formed in the setting portion 4 on an extension line of the band hole 5. A central interval between a band hole 5 selected appropriately from the ten band holes 5 and the setting hole 6 corresponds to the circumference of the loop formed by the wristband 1 when attached in loop form. Note that the number of band holes 5 and the number of setting holes 6 are not limited to the examples mentioned above, and may be increased or decreased appropriately if necessary.

Band hole displays 7 constituted by a sequence of numbers from 1 to 10, counting from the setting hole 6 side, are printed beside (below in the drawing) the band holes 5 in positions corresponding to the respective band holes 5. Further, a length measurement portion 8 is arranged parallel to the band holes 5 on the opposite side of the band holes 5 to the band hole displays 7 (above the band holes 5 in the drawing), and a starting point mark 9 indicating a lengthwise direction center position of the setting hole 6 is printed beside (above in the drawing) the setting hole 6 in the setting portion 4 on an extension line of the length measurement portion 8. Band hole displays 10 constituted by the same sequence of numbers as the band hole displays 7 provided beside the band holes 5 and boundary marks 11 indicating an application range of the respective band hole displays 10 are provided in the length measurement portion 8 at identical intervals to the intervals between the band holes 5. The boundary marks 11 are provided further toward the starting point mark 9 than the respectively corresponding band holes 5. Furthermore, a display depicting the words "setting hole" is printed on the display portion 2 side of the setting hole 6.

An interval between a length measurement portion closest portion 12, which is the portion of the length measurement portion 8 that is closest to the setting hole 6, and the starting point mark 9 is set to be shorter than a minimum circumference of a group of applied wrists and ankles for use in confirming the circumference of the wrist or the like, while an interval between a length measurement portion farthest portion 13, which is the portion farthest from the setting hole 6 on the opposite side to the length measurement portion nearest portion 12, and the starting point mark 9 is set to be longer than a maximum circumference of the group of applied wrists and ankles. In other words, when the wristband 1 according to this embodiment is applied widely to children and adults, the interval from the length measurement portion closest portion 12 closest to the setting hole 6 to the starting point mark 9 of the setting portion 4 is preferably somewhat shorter than the circumference of the wrist of a child having a short wrist circumference, while the interval from the length measurement portion farthest portion 13 farthest from the setting hole 6 to the starting point mark 9 is preferably set to be slightly longer than the circumference of the wrist of an adult having a long wrist circumference.

A difference between the interval from the band hole 5 to the setting hole 6 and the interval from the corresponding length measurement portion 8 to the starting point mark 9 is set as a margin from a state in which the wristband 1 is fitted closely to the wrist or ankle when the wristband 1 is attached in loop form to the wrist or ankle, and attachment comfort on the wrist or ankle is determined according to the length of this difference. Note, however, that the attachment comfort also varies according to the application, the attachment subject, the material of the wristband 1, and so on, and therefore this length is set appropriately in accordance with the object rather than being determined uniformly in all cases.

Further, the difference must be set within a smaller range than a minimum value of a difference between the circumference (minimum circumference) of the attachment subject wrist or ankle and the circumference (maximum circumference) of the hand or foot to ensure that the wristband 1 does not fall off the wrist or ankle to which it is attached.

Further, the interval between adjacent band holes 5 is preferably set narrowly such that minute adjustments can be made easily in accordance with the circumference of the wrist or ankle, and in a wristband 1 applied to a child having a small ankle or wrist circumference, the intervals between the band holes 5 provided near the setting hole 6 and between the boundary marks 11 provided near the starting point mark 9 are preferably set particularly narrowly to ensure easy adjustment.

As shown in FIG. 2, for example, the wristband 1 according to this embodiment may be cut out from a cutting line 14 or the like formed on a sheet base material 15 by means of perforations formed along an outline of the wristband 1 or so-called spot application processing[iii] in which a cutting portion is provided partially, whereby the wristband 1 can be set on a printer (not shown) and printing can be performed on the display portion 2. The band holes 5 and setting hole 6 are formed by implementing punching processing on the sheet base material 15. The sheet base material 15 is further formed with cutout perforations 16 allowing a single wristband 1 to be separated from another wristband 1 together with the sheet base material 15, which is convenient when the wristbands 1 are cut out and distributed in a required number following printing by the printer.

[iii] Please check this.

The phrase "printing advancement direction" and an arrow indicating a direction are printed on the sheet base material 15 in a blank space. The sheet base material 15 having this constitution is wound into a roll and attached to the printer, whereupon a "two-dimensional code", a department name "surgery", a ward number "East 02", a patient name "Taro Sato", a patient ID number "ID: 060805003", and so on are printed onto the display portion 2, as shown in FIG. 2. Note that the content of the printing may be modified to predetermined content in accordance with the object such that the wristband 1 can be used in a wide variety of applications such as an entrance ticket for an amusement park or an event.

There are no particular limitations on the material of the sheet base material 15 used in this embodiment, but to facilitate printing by the printer, a material that is suitable for printing by a printer and is neither uncomfortable nor obstructive when attached to the human body is selected. In medical applications, a film type base material such as synthetic paper, PET (polyethylene terephthalate), PE (polyethylene), PP (polypropylene), PS (polystyrene), and PVC (polyvinyl chloride), cloth, nonwoven fabric, a compound thereof, and so on, for example, are typically used due to the need for long-term use and resistance to chemicals such as water and alcohol. Further, in consideration of hygiene, the proliferation of harmful bacteria can be prevented by applying or incorporating an antibacterial agent.

At amusement parks, events, and so on, the use time is often short, and therefore water resistance and durability requirements are not particularly high. Therefore, in addition to the base materials mentioned above, a paper base material made of coated paper, art paper, or the like, or a compound thereof may be selected.

Figure 3:
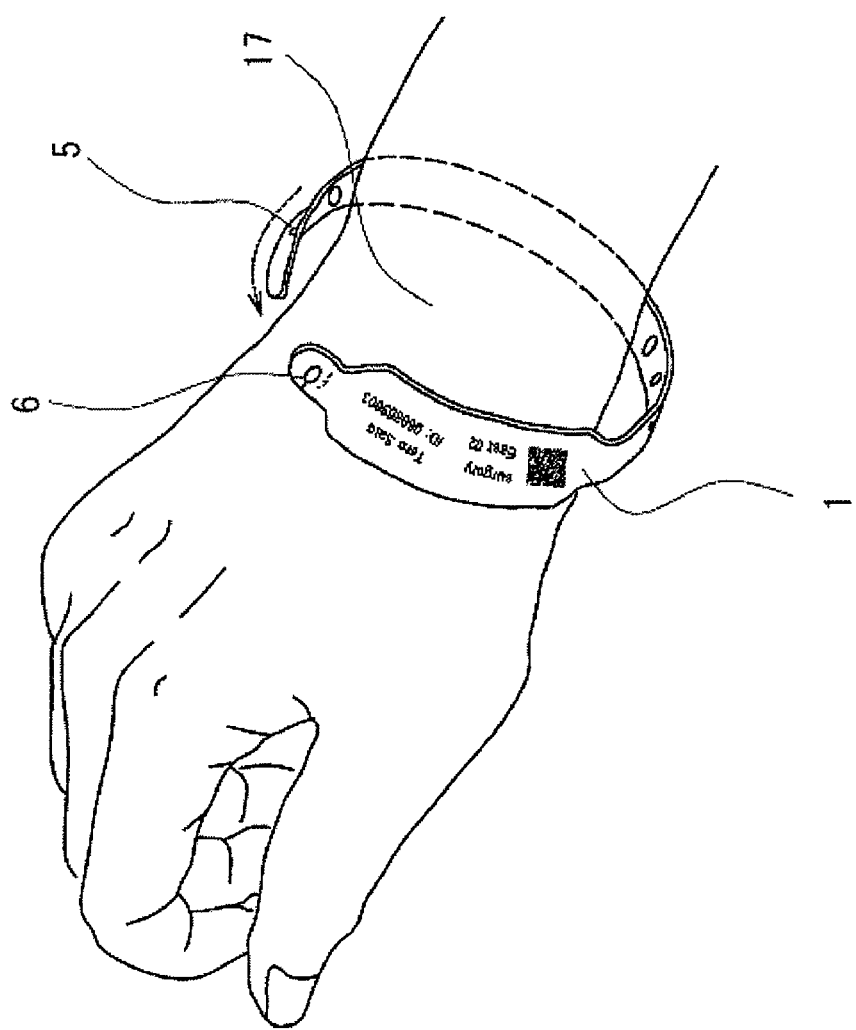
FIG. 3 is an illustrative view showing a state in which the wristband shown in FIG. 1 is attached to a wrist.
Figure 4:
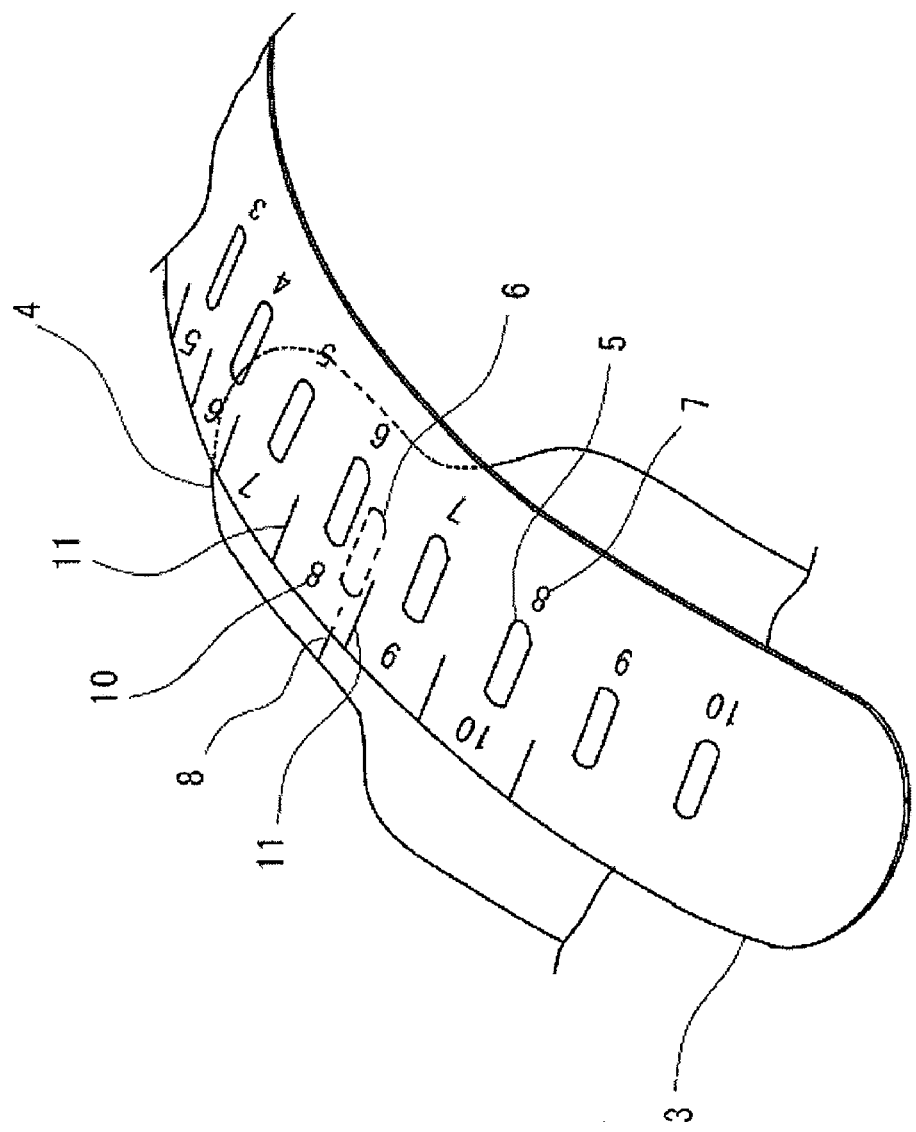
FIG. 4 is an illustrative view showing a method for selecting an optimum band hole by overlapping a band portion and a setting portion of the wristband shown in FIG. 1.
Figure 5:
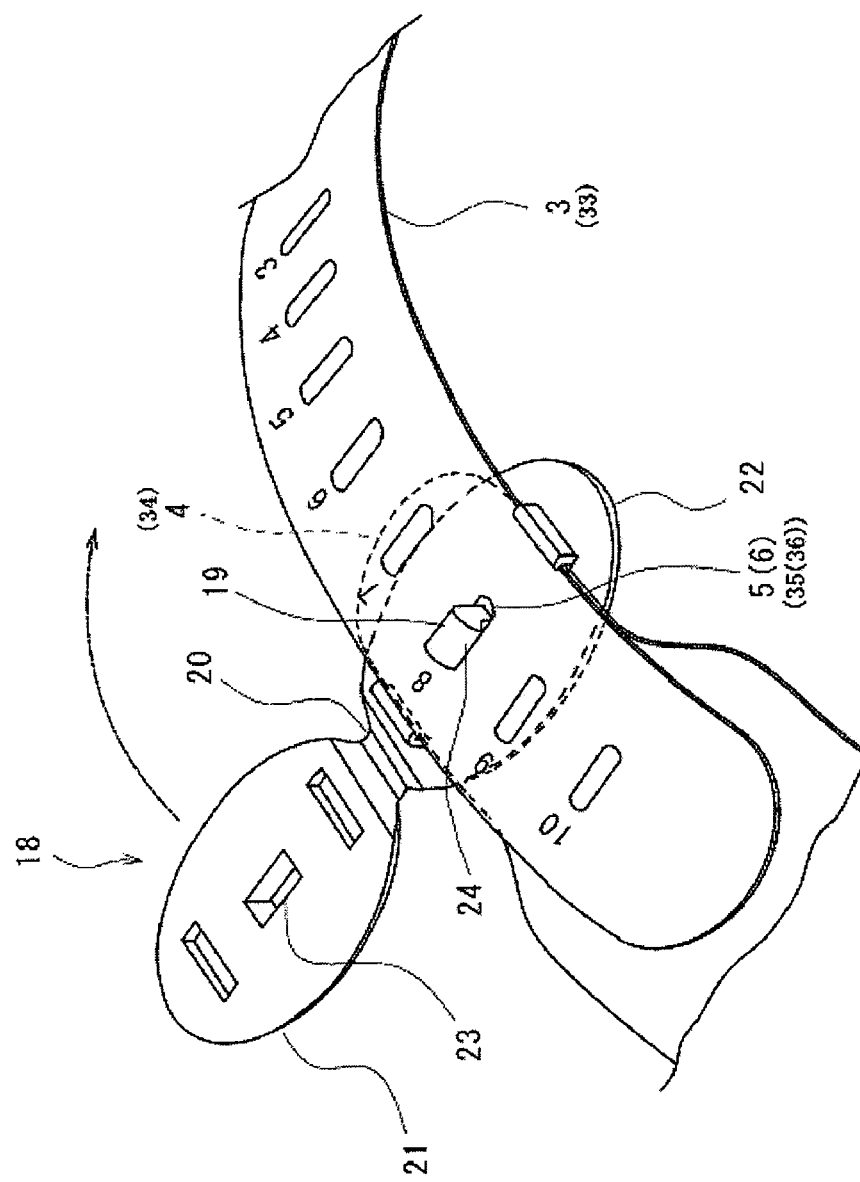
FIG. 5 is an illustrative view showing insertion of a wristband clip into the band hole and a setting hole.
Figure 6:
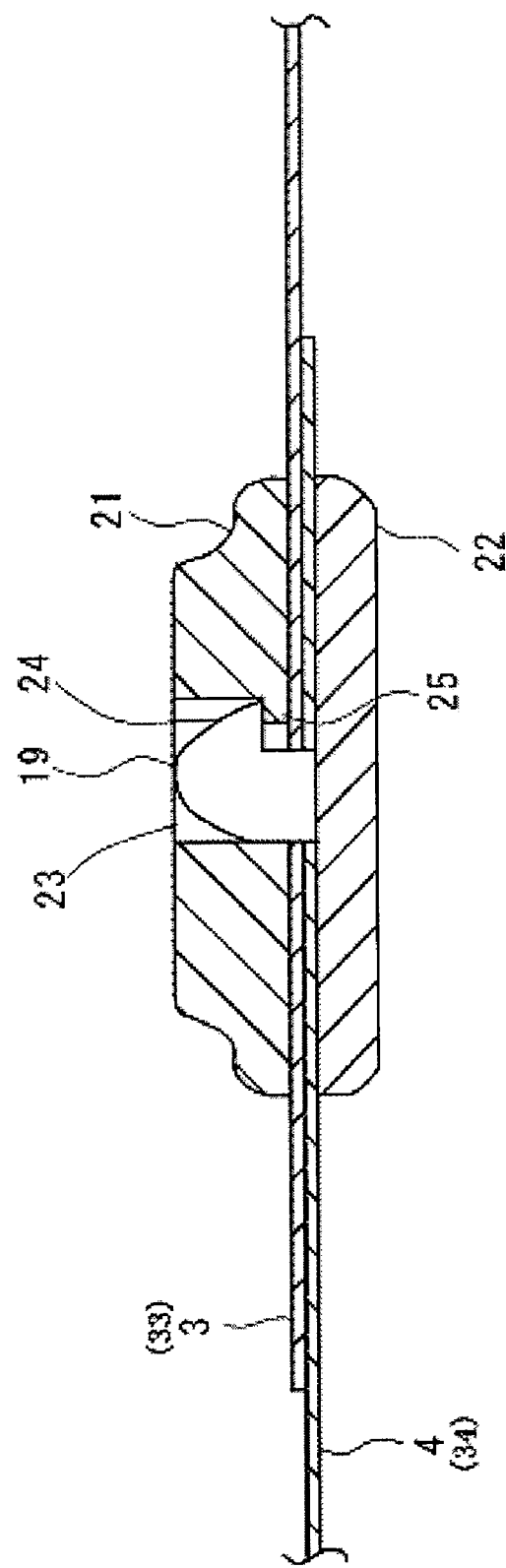
FIG. 6 is a partial sectional view showing a state in which the band hole and the setting hole are latched by the wristband clip.

Next, a method of attaching the wristband 1 according to this embodiment to a wrist will be described. FIG. 3 is an illustrative view showing a state in which an embodiment of the wristband 1 according to the present invention is attached to a wrist. FIG. 4 is an illustrative view showing a method for selecting an optimum band hole by overlapping the band portion and the setting portion. FIG. 5 is an illustrative view showing insertion of a wristband clip 18 into the band hole 5 and the setting hole 6. FIG. 6 is a partial sectional view showing a state in which the band portion 3 and the setting portion 4 are latched by the wristband clip 18.

To attach the wristband 1 to a wrist 17, first, the wristband 1 is wound around the wrist 17 of a patient or the like, and when the wristband 1 is optimally fitted to the wrist 17, the number of the corresponding band hole display 10 is confirmed from the range of the boundary mark 11 overlapping the starting point mark 9 of the length measurement portion 8. By selecting the band hole 5 having the band hole display 7 of the same number as the band hole display 10, the band hole 5 to be combined with the setting hole 6 is determined. In FIG. 4, for example, the starting point mark 9 is within the range of the boundary mark 11 of the band hole display 10 having the number "8", and therefore the band hole 5 having the number "8" is selected as a latch partner. The band hole 5 selected as appropriate for the patient or the like is then aligned with the setting hole 6, and a latch portion 19 of the wristband clip 18 is inserted therein and temporarily latched. Note that in FIG. 5, attachment is performed with the rear surface of the band portion 3 overlapping the front surface of the setting portion 4, but the rear surface of the setting portion 4 and the rear surface of the band portion 3 may be overlapped.

Next, the wristband clip 18 is bent back from the position of a hinge 20 in the direction of an arrow, whereupon a female clip portion 21 is aligned with a male clip portion 22 and the latch portion 19 is pressed into a latch hole 23 formed in the female clip portion 21. As a result, a tip end part of a pawl portion 24 decreases in width due to an elastic force thereof such that the latch portion 19 is completely inserted into the latch hole 23. Thus, latching is performed as shown in FIG. 5. Once the latch portion 19 is inserted into the latch hole 23, the tip end part of the pawl portion 24 increases in width due to a restoring force thereof, and as a result, the latch portion 19 is prevented from becoming dislodged by a projecting portion 25.

Next, a second embodiment of the present invention will be described using FIGS. 7 and 8. Note that identical constitutional elements to those described above have been allocated identical reference numerals, and description thereof has been omitted.

Further, with regard to FIGS. 5 and 6, the second embodiment is substantially identical to the first embodiment, and therefore FIGS. 5 and 6 will be described using the reference numerals shown in parentheses in the drawings where appropriate.

Figure 7:
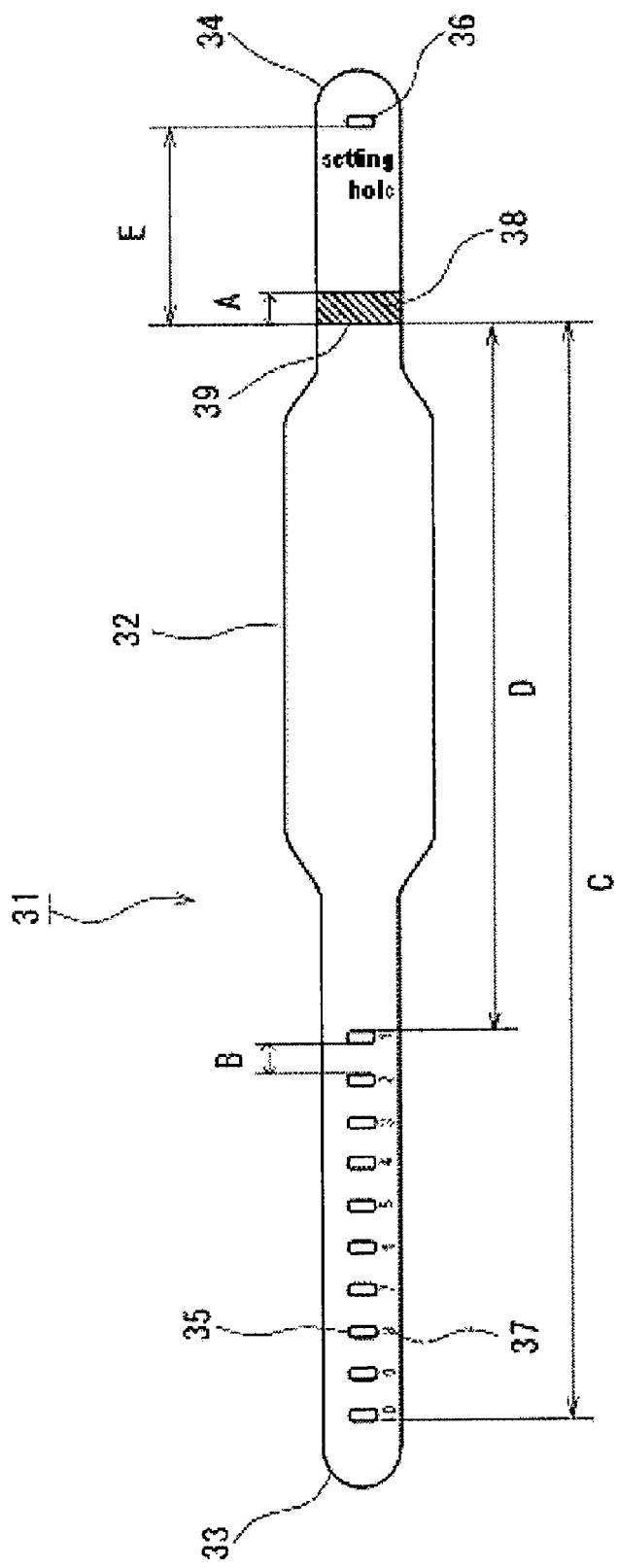
FIG. 7 is a plan view showing the constitution of a wristband according to a second embodiment of the present invention.

FIG. 7 is a plan view showing the constitution of a second embodiment of the wristband according to the present invention. FIG. 8 is a plan view showing an example of use of the wristband shown in FIG. 7.

Referring to FIG. 7, a wristband 31 according to this embodiment includes a display portion 32 for displaying information relating to the patient or the like in the center thereof. A band portion (one end portion) 33 to be wrapped around the wrist or the like is provided on one end of the display portion 32, and a setting portion (other end portion) 34 that allows the wristband 31 to be attached in loop form when a tip end thereof overlaps the band portion 33 is provided on the other end of the display portion 32. The band portion 33 and the setting portion 34 both extend from the display portion 32 in a lengthwise direction. Further, ten band holes 35 are formed in the band portion 33 at equal lengthwise direction intervals, and a single setting hole 36 is formed in the setting portion 34. An interval between a band hole 35 selected appropriately from the ten band holes 35 and the setting hole 36 corresponds to the circumference of the loop formed by the wristband 31 when attached in loop form. Band hole numbers 37 constituted by a sequence of numbers from 1 to 10, counting from the setting hole 36 side, are displayed beside (below in the drawing) the band holes 35 in accordance with the respective band holes 35, and a display of the phrase "setting hole" is printed beside (to the left of in the drawing) the setting hole 36.

A strip-form identification display portion 38 is printed on the setting portion 34 over the entire width of the setting portion 34 such that when the band portion 33 is overlapped onto the setting portion 34 and the identification display portion 38 is viewed through the band hole 35, it can be identified as a ground color of the wristband 31. The identification display portion 38 may be printed in a solid color over the entire region thereof, but by setting the size of the ground color part to be smaller than the band hole 35, pattern printing may also be selected[iv]. Further, the identification display portion 38 does not necessarily have to be provided over the entire width, and the form thereof is not limited to a strip form. However, to ensure visibility through the band hole 35, the identification display portion 38 is preferably formed to include a center line linking the band holes 35 from at least the setting hole 36[v].

[iv] Please check.
[v] Please check.

The band hole 35 side of the identification display portion 38 forms a reference line 39 that serves as a reference when comparing and verifying the circumference of the wrist or the between the band holes 35. Further, a lengthwise direction length (A) of the identification display portion 38 is set to be identical to an interval (B) between adjacent band holes 35. Hence, when the wristband 31 is wrapped around the wrist such that the band portion 33 overlaps the setting portion 34, the identification display portion 38 is invariably displayed through one of the band holes 35. Note, however, that as long as the position of the reference line 39 can be confirmed, the identification display portion 38 achieves its object, and therefore, for practical purposes, the lengthwise direction length (A) of the identification display portion 38 may be set longer. For example, the identification display portion 38 may be printed over the entire setting portion 34 from the reference line 39 to the end portion of the setting portion 34.

Further, an interval (C) between the band hole 35 farthest from the setting hole 36 to the reference line 39 is set to be greater than the maximum circumference of the group of wrists and so on envisaged as the attachment subject, whereas an interval (D) between the band hole 35 closest to the setting hole 36 and the reference line 39 is set to be shorter than the minimum circumference of the group of wrists and so on envisaged as the attachment subject. For example, when the wristband 31 is attached to the wrists of subjects ranging from infants to adults, the interval (C) and the interval (D) are set to be longer than the wrist circumference of the adult having the greatest wrist circumference and shorter than the wrist circumference of the infant having the shortest wrist circumference. Hence, when the wristband 31 is wrapped around the wrist such that the band portion 33 overlaps the setting portion 34, the position in which the band portion 33 overlaps the reference line 39 is located between the band hole 35 closest to the reference line 39 and the band hole 35 farthest from the reference line 39.

Further, the interval (B) between adjacent band holes 35 is set to be smaller than an interval (E) from the setting hole 36 to the reference line 39. By setting the intervals between the band holes 35 to be narrow, the band hole 35 that is latched to the setting hole 36 can be shifted in minute increments from the optimum band hole 35 selected in a manner to be described below to a long circumference side or a short circumference side according to preference.

The interval (E) from the setting hole 36 to the reference line 39 corresponds to a circumference margin from the wrist or the like, and is set to be smaller than a maximum-minimum circumference difference at which the wristband 31 can be attached to the wrist or the like without falling off the hand or the like, or more specifically a difference between the circumference (maximum circumference) when the wristband 31 is wrapped around a maximum circumference part such as the palm of the hand and the circumference (minimum circumference) when the wristband 31 is wrapped around a minimum circumference part such as the wrist. The value of this difference is typically smaller in a child, and therefore, when a child is the attachment subject, the value is set in consideration of the hand of a child. Further, the interval from the setting hole 36 to the reference line 39 affects fitting comfort when the wristband 31 is attached to the wrist or the like, and therefore the interval is set at the most comfortable interval within the above range.

Figure 8:
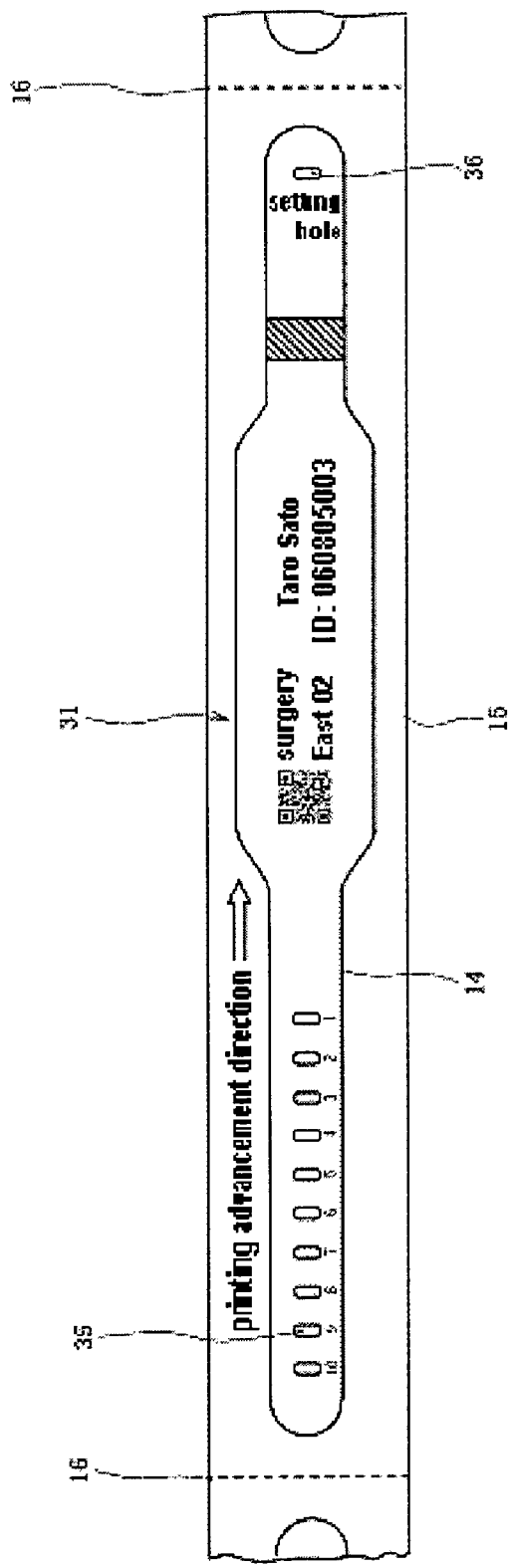
FIG. 8 is a plan view showing an example of use of the wristband shown in FIG. 7.

As shown in FIG. 8, for example, the wristband 31 according to this embodiment may be cut out from the cutting line 14 formed on the sheet base material 15 by means of perforations 16 formed along the outline of the wristband 31 or so-called spot application processing in which a cutting portion is provided partially, whereby the wristband 31 can be set on a printer (not shown) and printing can be performed on the display portion 32. The band holes 35 and setting hole 36 are formed by implementing punching processing on the sheet base material 15. The sheet base material 15 is further formed with the cutout perforations 16 allowing a single wristband 31 to be separated from another wristband 31 together with the sheet base material 15, which is convenient when the wristbands 31 are cut out and distributed in a required number following printing by the printer. Further, the phrase "printing advancement direction" and an arrow indicating a direction are printed on the sheet base material 15 in a blank space. The sheet base material 15 having this constitution is wound into a roll and attached to the printer, whereupon a "two-dimensional code", a department name "surgery", a ward number "East 02", a patient name "Taro Sato", a patient ID number "ID: 060805003", and so on are printed onto the display portion 32, for example. Note that the content of the printing may be modified to predetermined content in accordance with the object such that the wristband 31 can be used in a wide variety of applications such as an entrance ticket for an amusement park or an event.

Figure 9:
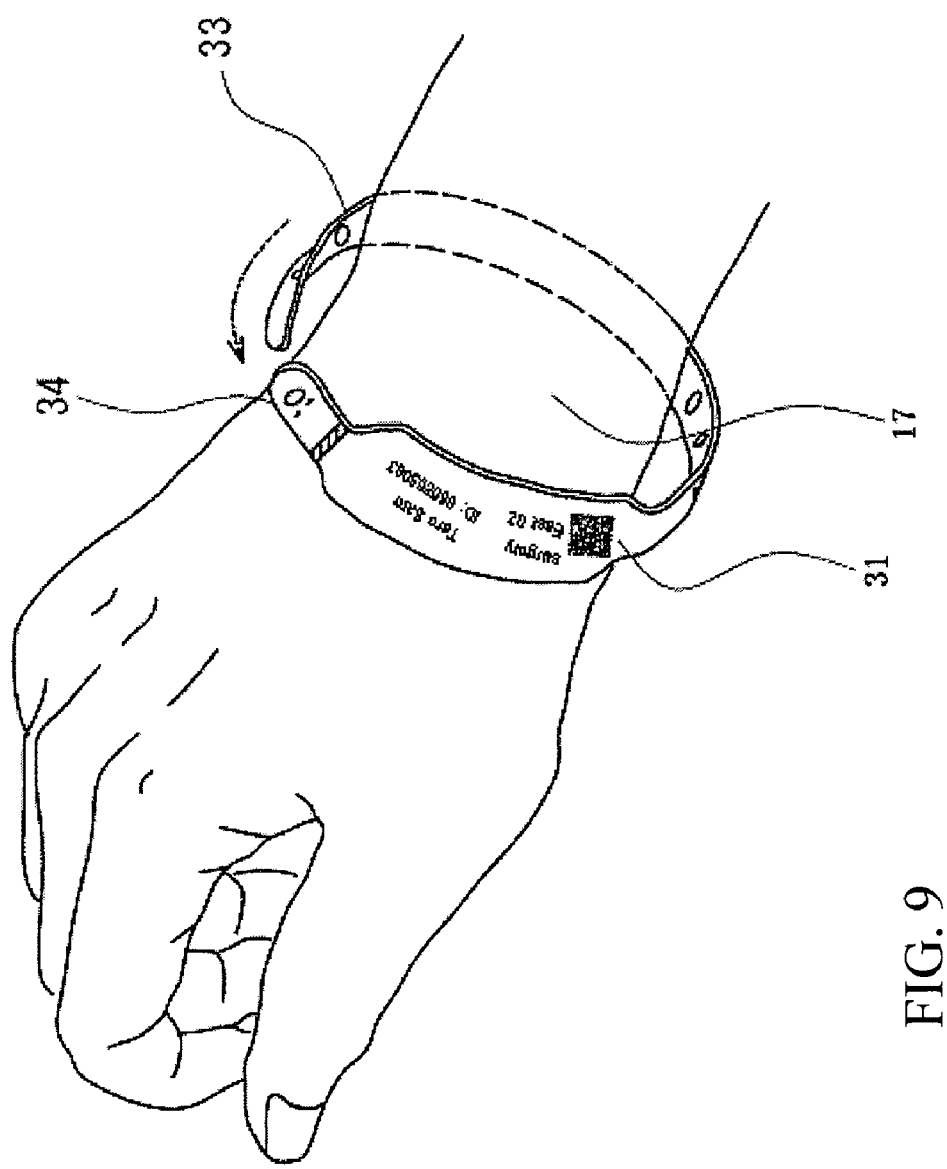
FIG. 9 is an illustrative view showing a state in which the wristband shown in FIG. 7 is attached to a wrist.
Figure 10:
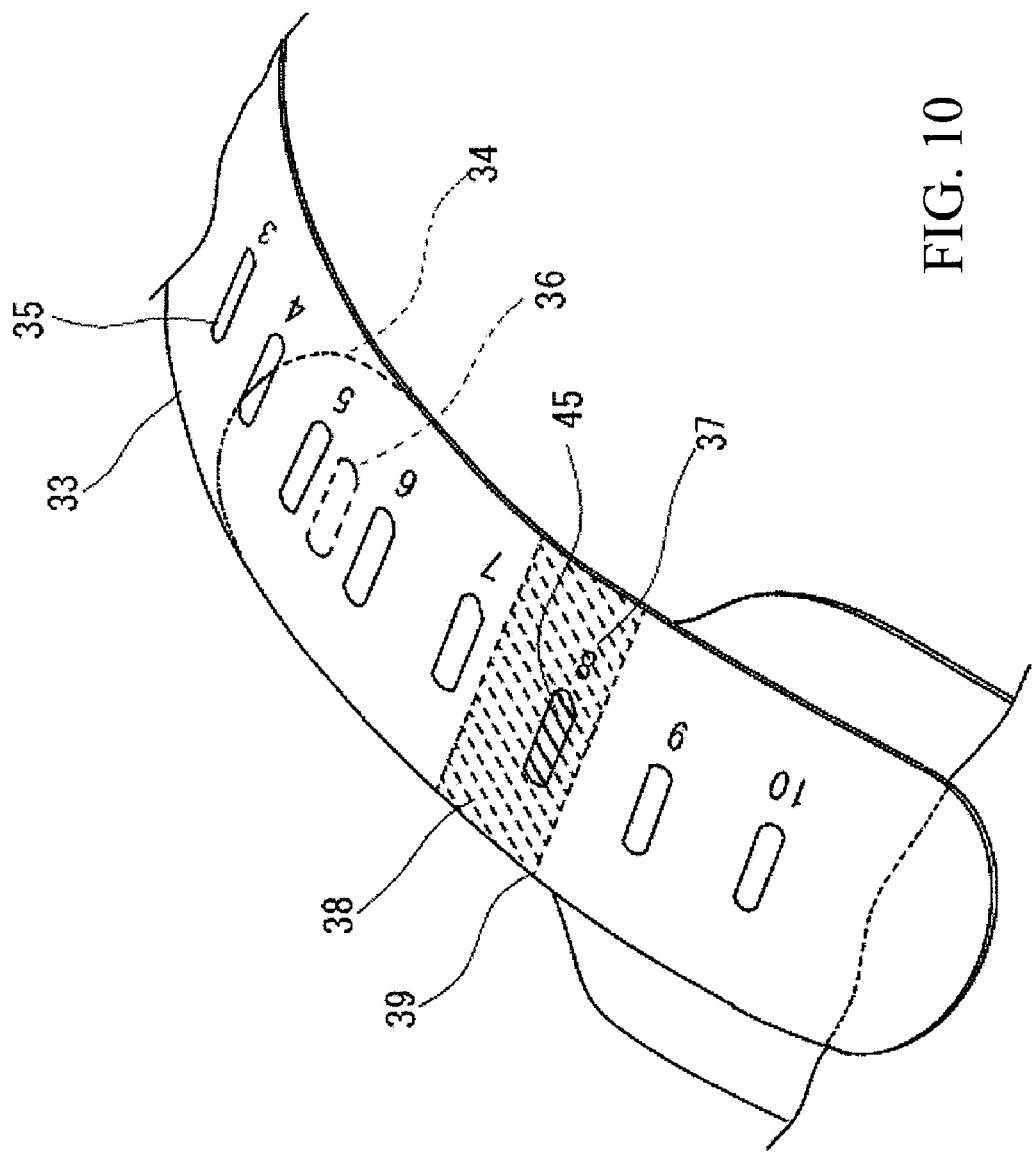
FIG. 10 is an illustrative view showing a method for selecting an optimum band hole by overlapping a band portion and a setting portion of the wristband shown in FIG. 7.

Next, a method of attaching the wristband 31 according to this embodiment to a wrist will be described. As shown in FIG. 9, the wristband 31 is wrapped around the wrist 17, and as shown in FIG. 10, the optimum band hole 35 is selected by overlapping the band portion 33 and the setting portion 34, similarly to the first embodiment described above. Then, as shown in FIG. 5, the wristband clip 18 is inserted into the band hole 35 and setting hole 36, and as shown in FIG. 6, the band portion 33 and setting portion 34 are latched by the wristband clip 18.

To attach the wristband 31 to the wrist 17, first, the wristband 31 is wrapped around the wrist 17 of the patient or the like such that the band portion 33 overlaps the setting portion 34 (overlapping step). A band hole number 37 of a band hole 45 through which the identification display portion can be seen when the wristband 31 is optimally fitted to the wrist 17 is then confirmed (confirmation step). In this embodiment, the lengthwise direction length of the identification display portion 38 is set to be identical to the interval between adjacent band holes 35, and therefore, when the wristband 31 is wrapped around the wrist 17 such that the band portion 33 overlaps the setting portion 34, the identification display portion 38 is always displayed through only one band hole 35. Note that the identification display portion 38 may be provided over the entire setting portion 34 from the reference line 39 to the end portion of the setting portion 34, and in this case, the identification display portion 38 is displayed through a plurality of the band holes 35. Accordingly, the band hole 35 farthest from the setting hole 36 (the band hole 35 closest to the reference line 39) is selected.

Next, the wristband 31 is loosened slightly and the wristband clip 18 is inserted into the band hole 35 corresponding to the band hole number 37 confirmed as described above and the setting hole 36. The operation described above with reference to FIG. 5 is then performed such that latching is achieved as shown in FIG. 6 (latching step).

Note that the present invention is not limited to the embodiments described above, and each embodiment may be subjected to appropriate modifications within the scope of the technical spirit of the present invention. Furthermore, the numbers, positions, shapes and so on of the constitutional members described above are not limited to those of the embodiments described above, and may be set appropriately in order to implement the present invention.

Figure 11:
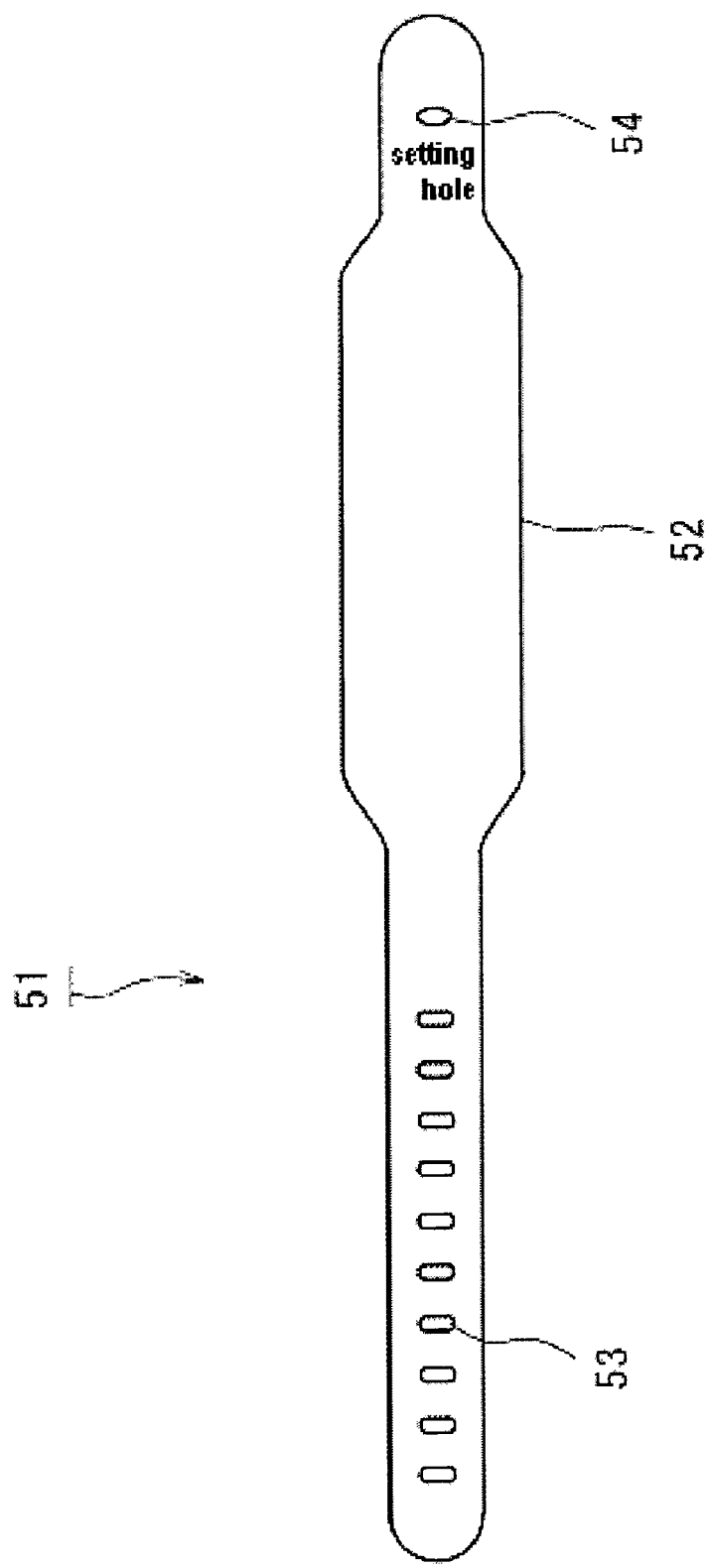
FIG. 11 is a plan view showing a conventional wristband.

FIG. 1
SETTING HOLE
FIG. 2
PRINTING ADVANCEMENT DIRECTION
SURGERY
EAST 02
TARO SATO
SETTING HOLE
FIG. 3
SURGERY
EAST 02
TARO SATO
SETTING HOLE
FIG. 7
SETTING HOLE
FIG. 8
PRINTING ADVANCEMENT DIRECTION
SURGERY
EAST 02
TARO SATO
SETTING HOLE
FIG. 9
SURGERY
EAST 02
TARO SATO
SETTING HOLE
FIG. 11
SETTING HOLE

Translator's note:

What is claimed is:

1. A band of a strip-form base material including
   a first end portion of the band, a plurality of band holes formed in the first end portion of the band at predetermined intervals along one lengthwise direction of the end portion,
   a center area of the band operable as a display portion,
   a second end portion of the band, a setting hole formed in the second end portion,
   the band being bendable in loop form to be held in that form by a device at the band hole and the setting hole, and
   an aligning device on the band for matching a length between the setting hole and a band hole to set a circumference for the loop form,
   the aligning device having a length measurement portion, the length measurement portion extending on a parallel line to the band holes in the first end portion, the band holes being respectively associated with the length measurement portion such that each individual band hole is referenced individually to a marked portion of the length measurement portion, and the band holes are so placed that an interval from each of the band holes to the setting hole is set to be longer, by a predetermined length, than an interval from the marked portion of the length measurement portion corresponding to each band hole to a starting point portion set in the second end portion on a line of extension from the length measurement portion.

2. The band according to claim 1, further comprising a band hole display including a number or a symbol in the vicinity of each of the band holes and being of a type to identify the respective band holes,
   the band hole display is in the length measurement portion, and
   the band holes and the length measurement portion are associated referably via the band hole display.

3. The band according to claim 2, wherein the band hole display in the length measurement portion is defined by a boundary mark indicating a boundary thereof or by color coding.

4. The band according to claim 1, wherein a first interval from the starting point portion to a closest portion thereto of the length measurement portion is set to be shorter than a minimum value of a selected circumference of an object on which the band is positioned, and a second interval from the starting point portion to a farthest portion therefrom of the length measurement portion is set to be longer than a maximum value of the selected circumference of the object on which the band is positioned.

5. The band according to claim 1, wherein a difference between an interval from the band hole to the setting hole and an interval from the length measurement portion associated therewith to the starting point portion is set to be smaller than a difference between a selected first and a selected second circumference of the object on which the band is positioned.

6. The band according to claim 1, wherein the starting point portion is a mark indicating a central position of the setting hole.

7. The band of claim 1, wherein the device at the band hole and the setting hole is a wristband clip into the holes.

8. The band of claim 1, wherein the band is a wristband.

9. A method of using a band, comprising
   providing a band of a strip-form base material including
   a first end portion of the band, a plurality of band holes formed in the first end portion of the band at predetermined intervals along one lengthwise direction of the end portion,
   a center area of the band operable as a display portion,
   a second end portion of the band, a setting hole formed in the second end portion,
   the band being bendable in loop form to be held in that form by a device at the band hole and the setting hole, and
   an aligning device on the band for matching a length between the setting hole and a band hole to set a circumference for the loop form;
   the aligning device having a length measurement portion and the length measurement portion extending on a parallel line to the band holes in the first end portion, the band holes being respectively associated with the length measurement portion such that each individual band is referenced individually to a marked portion of the length measurement portion, and the band holes are so placed that an interval from each of the band holes to the setting hole is set to be longer, by a predetermined length, than an interval from the marked portion of the length measurement portion corresponding to each band hole to a starting point portion set in the second end portion on a line of extension from the length measurement portion, the method further comprising the steps of:

overlapping the first end portion and the second end portion by wrapping the band around a wrist or an ankle;

selecting the band hole display corresponding to the length measurement portion that overlaps the starting point portion at a minimum circumference; and latching the band to the wrist or ankle by inserting a band clip into the band hole corresponding to the selected band hole display and the setting hole.

10. The band according to claim 1, wherein the aligning device comprises a reference line provided in the second end portion at a predetermined distance from the band holes for comparing and verifying the circumference of the object on which the band is positioned between the band holes; and an identification display portion provided in the direction of the setting portion from the reference line at a length that is equal to or greater than an interval between adjacent band holes so as to be identifiable through the band holes.

11. The band according to claim 10, wherein a first interval between the band hole farthest from the setting hole and the reference line is set to be larger than a maximum circumference of the object on which the band is positioned.

12. The band according to claim 10, wherein a second interval between the band hole closest to the setting hole and the reference line is set to be smaller than a minimum circumference of the object on which the band is positioned.

13. The band according to claim 10, wherein the object on which the band is positioned is a wrist or ankle and a third interval between the setting hole and the reference line is set to be smaller than a maximum-minimum circumference difference of a hand or a foot at which the band can be attached to the wrist or the ankle without falling off the hand or the foot.

14. The band according to claim 10, wherein the interval between adjacent band holes is smaller than the interval between the setting hole and the reference line.

15. A method of using the band comprising providing a strip-form base material band including a first end portion of the band, a plurality of band holes formed in the first end portion of the band at predetermined intervals along one lengthwise direction of the end portion, a center area of the band operable as a display portion, a second end portion of the band, a setting hole formed in the second end portion, the band being bendable in loop form to be held in that form by a device at the band hole and the setting hole, and an aligning device on the band for matching a length between the setting hole and a band hole to set a circumference for the loop form;

the aligning device comprises a reference line provided in the second end portion at a predetermined distance from the band holes for comparing and verifying the circumference of the object on which the band is positioned between the band holes; and an identification display portion provided in the direction of the setting portion from the reference line at a length that is equal to or greater than an interval between adjacent band holes so as to be identifiable through the band holes;

the method further comprises the steps of:

overlapping the first end portion and the second end portion at a minimum circumference by wrapping the band around an object on which the band is positioned;

confirming the farthest band hole from the setting hole through which the identification display portion is displayed for identification; and latching the band to an object on which the band is positioned by a latching device at the confirmed band hole and the setting hole.

16. The method according to claim 15, wherein the latching device comprises a wristband clip and inserting the clip into the confirmed band hole and the setting hole.

* * * * *